United States Patent
Krentz

(10) Patent No.: US 6,355,262 B1
(45) Date of Patent: Mar. 12, 2002

(54) LINIMENT FOR TOPICAL APPLICATION

(76) Inventor: Sigmund Krentz, 10747 Mapleshire Cr. SE., Calgary (CA), T2J 1Z1

( * ) Notice: Subject to any disclaimer, the term of this patent is extended or adjusted under 35 U.S.C. 154(b) by 0 days.

(21) Appl. No.: 09/652,602

(22) Filed: Aug. 30, 2000

Related U.S. Application Data

(60) Provisional application No. 60/151,376, filed on Aug. 30, 1999.

(51) Int. Cl.[7] ................................................. A61K 7/48
(52) U.S. Cl. ..................... 424/401; 424/489; 514/944; 514/969
(58) Field of Search ..................... 424/400, 401, 424/489, 725; 514/969, 944

(56) References Cited

U.S. PATENT DOCUMENTS

| | | | |
|---|---|---|---|
| 5,248,504 A | 9/1993 | Friedman | 424/434 |
| 5,385,734 A | 1/1995 | Friedman | 424/434 |
| 6,015,233 A | * 4/2000 | Champon | 424/195.1 |

* cited by examiner

*Primary Examiner*—Thurman K. Page
*Assistant Examiner*—P. McQueeney
(74) *Attorney, Agent, or Firm*—David S. Thompson

(57) ABSTRACT

A liniment is disclosed for use in conjunction with massage or other manual topical application method, and is adapted for any application where massage therapy is used as a part of a medically recommended treatment, particularly where pain management is involved. The liniment for topical application includes a mixture of ethyl alcohol, methyl hydrate and distilled water. To this solution is added horseradish and powdered cayenne pepper. The mixture is sealed for 25 days, with twice daily stirring or shaking. The particulate matter is allowed to settle for 3 days, after which the liniment is siphoned off for use. The liniment may be applied topically to the skin in areas of pain and discomfort.

3 Claims, 1 Drawing Sheet

LINIMENT FOR TOPICAL APPLICATION

CROSS-REFERENCES

Figure 1:
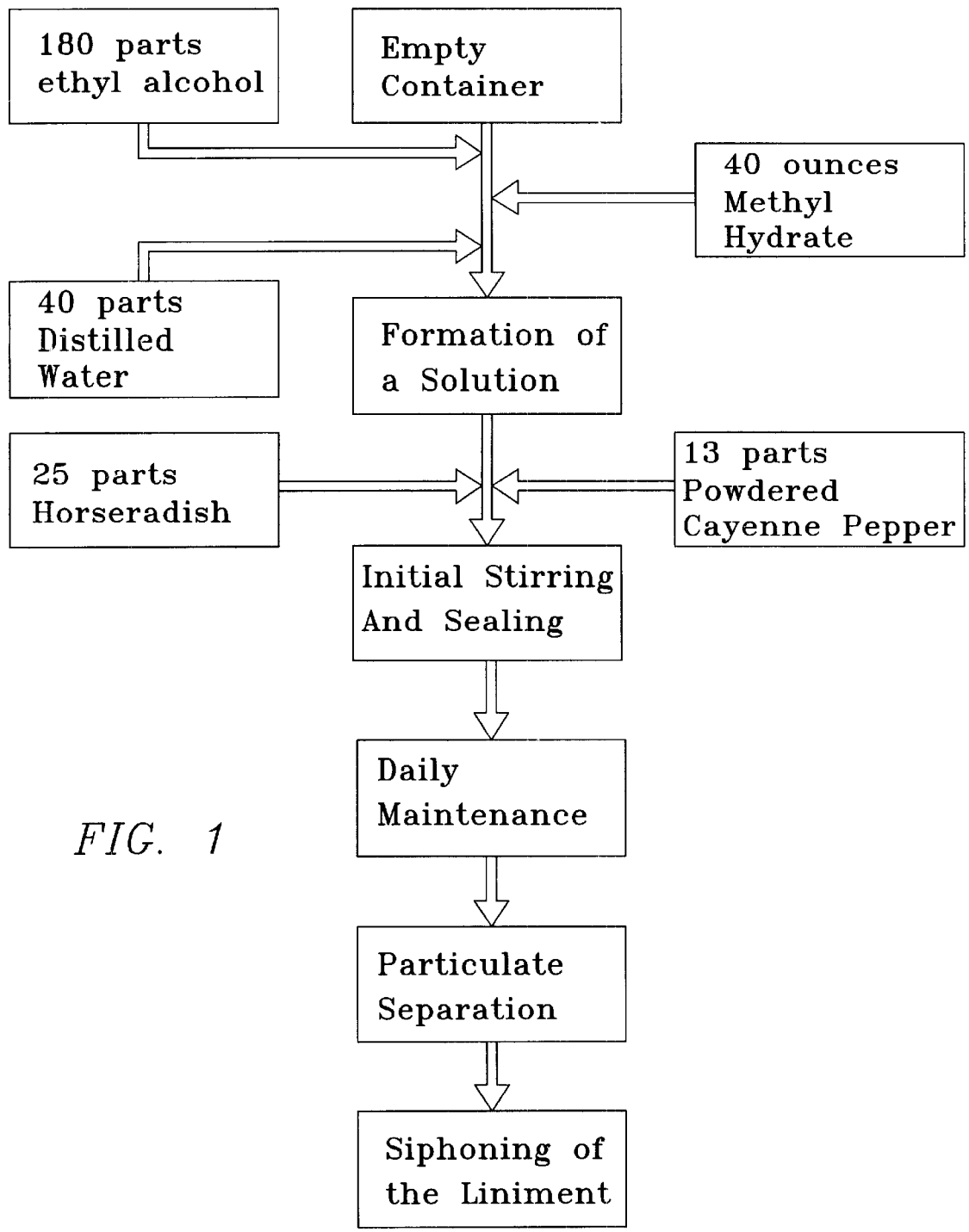

This application is a continuation of a provisional application having Ser. No. 60/151,376 filed Aug. 30, 1999.

BACKGROUND

A large number of people suffer from pain and disability due to rheumatoid arthritis, bursitis, and other sources of muscular, back and arthritic pain. As a result, a number of treatments have been developed in an attempt to provide relief to the millions of those who suffer.

However, despite the motivation of the many researchers, and the time and money that has been devoted to finding a treatment, no satisfactory treatment has been developed.

For the foregoing reasons, there is a need for a liniment for topical application, such as a liniment for use with massage, that will aid in the relief of the pain associated with rheumatoid arthritis, other forms of arthritis, bursitis and other related types of muscle ache and joint pain.

SUMMARY

The present invention is directed to a liniment that satisfies the above needs. The liniment of the present invention provides some or all of the following ingredients and is prepared in the following manner.
(A) A solution is formed in an appropriately sized container from the following, in the relative amounts:
   (a) 180 ounces of ethyl alcohol;
   (b) 40 ounces of methyl hydrate; and
   (c) 40 ounces of distilled water.
(B) The following ingredients are added to the solution:
   (a) 25 ounces of horseradish; and
   (b) 13 ounces of powdered cayenne pepper.
(C) The mixture is stirred well and the container is sealed with a lid.
(D) The container is agitated by stirring or shaking twice daily for 25 days.
(E) The container is then left in a stationary condition for three days, during which time the pulp or particulate matter is allowed to settle.
(F) The clear solution, which is the liniment, is then siphoned off for use. (G) To use, the liniment is applied topically to skin adjacent to the area of pain. The liniment results in a sensation of heat, which tends to sooth away pain and soreness. The application may continue to be effective for as much as 24 hours, and may be used to treat arthritis, rheumatoid arthritis, bursitis, sore muscles, back pain and other ailments.

It is therefore a primary advantage of the present invention to provide a novel liniment for topical application that is adapted for use with massage and other methods of topical application.

Another advantage of the present invention is to provide a novel liniment for topical application that is easily manufactured of low-cost ingredients.

A still further advantage of the present invention is to provide a novel liniment for topical application that encourages and facilitates users to treat muscle, joint and arthritic ache, soreness and pain with massage or a similar manual rubbing motion that results in relaxation as well as stress and pain reduction.

These and other features, aspects, and advantages of the present invention will become better understood with reference to the following description and appended claims.

DRAWINGS

These and other features, aspects, and advantages of the present invention will become better understood with regard to the following description, appended claims, and accompanying drawings where:

FIG. 1 is a diagram representing the process by which the liniment is manufactured.

DESCRIPTION

A liniment for use in combination with massage therapy and other methods of manual topical application includes a mixture of ethyl alcohol, methyl hydrate and distilled water. To this solution is added horseradish and powdered cayenne pepper. The mixture is sealed for 25 days, with twice daily stirring or shaking. The particulate matter is allowed to settle for 3 days, after which the liniment is siphoned off for use. The liniment may be applied topically to the skin, typically with massage, in areas of pain and discomfort. A sensation of heat may be felt as the liniment and massage therapy reduce pain and/or other discomfort. The benefit tends to last for as much as 24 hours, and over time some cumulative benefits may last indefinitely.

An initial solution is formed in an appropriately sized container from the following ingredients:
   (a) 180 parts of ethyl alcohol;
   (b) 40 parts of methyl hydrate; and
   (c) 40 parts of distilled water.

It should be noted that the absolute amounts of the ingredients is not so important as the relative amounts. That is, the amount of ethyl alcohol should be roughly 4.5 times the volume of the methyl hydrate and distilled water. Also, the amounts of each initial ingredient may be varied somewhat. The ethyl alcohol may be varied between 140 and 220 parts, and the methyl hydrate and distilled water may be varied between 30 and 50 parts, while still in retaining many of the benefits of the preferred percentages.

Additional ingredients are then added to the solution, including 25 parts of horseradish and 13 parts of powdered cayenne pepper. The exact amounts of these ingredients may be varied somewhat; however, the amounts should be selected at approximately these levels. Where substitution is desired, it is recommended that between 15 and 40 parts horseradish and 6 and 20 parts powdered cayenne pepper be used.

An initial stirring and sealing process is then followed. The mixture should then be stirred well initially, to result in a more homogeneous nature. Following stirring, the container should be sealed with an airtight lid. The airtight lid better preserves the mixture and to allows the mixture to be shaken.

A daily maintenance schedule is followed. The container is agitated by stirring or shaking twice daily for 25 days. Such shaking tends to enhance and speed chemical reactions which are occurring over time within the container. While 25 days is the preferred period, any period from 10 to 40 days could be substituted with some of the advantages seen with a 25-day period.

Following the conclusion of the daily maintenance schedule, the particulates are allowed to separate. The container is left in a stationary condition for three days, during which time the pulp or particulate matter is allowed to settle. This time is somewhat variable, because most of the particulate matter tends to sink fairly rapidly. As a result, any period from 1 to 5 days, or more, could be substituted for similar results, although 3 days is preferred, and gives the best results.

The liniment is then siphoned out of the container. The clear solution at the top of the container is the liniment. The liniment is then siphoned off for storage and later use. Siphoning is the preferred method of liniment removal, because it tends to leave the pulp and particulate matter undisturbed in a lower portion of the container. However, the liniment could alternatively be poured off, without excessive disturbance of the pulp and particulate matter. If desired, filtration may be used to prevent transfer of the pulp and particulate matter.

To use, the liniment is applied topically to skin adjacent to the area of pain. The liniment results in a sensation of heat, and tends to sooth away pain and soreness.

The application may continue to be effective for as much as 24 hours, although the effects of cumulative applications of the liniment may in some applications continue to be effective almost indefinitely.

The liniment may be used to treat arthritis, rheumatoid arthritis, bursitis, sore muscles, back pain and other ailments, and is indicated in any application where it may be used in conjunction with massage therapy in the course of medically recommended treatment.

The previously described versions of the present invention have many advantages, including a primary advantage of providing a novel liniment for topical application that is adapted for use with massage and other methods of topical application.

Another advantage of the present invention is to provide a novel liniment for topical application that is easily manufactured of low-cost ingredients.

A still further advantage of the present invention is to provide a novel liniment for topical application that encourages and facilitates users to treat muscle, joint and arthritic ache, soreness and pain with massage or a similar manual rubbing motion that results in relaxation as well as stress and pain reduction.

The invention resides not in any one of these features per se, but rather in the particular combination of all of them herein disclosed and claimed and it is distinguished from the prior art in this particular combination of all of its structures for the functions specified.

Although the present invention has been described in considerable detail and with reference to certain preferred versions, other versions are possible. For example, while preferred percentages of the different ingredients have been disclosed, some modification of the ratios between the ingredients, or the addition of inert ingredients, could be resorted to while still in keeping within the teachings of the invention. Therefore, the spirit and scope of the appended claims should not be limited to the description of the preferred versions disclosed.

In compliance with the U.S. Patent Laws, the invention has been described in language more or less specific as to methodical features. The invention is not, however, limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

What is claimed is:

1. A liniment for topical application, the liniment comprising:
   (A) 90 to 270 parts ethyl alcohol;
   (B) 20 to 60 parts methyl hydrate;
   (C) 20 to 60 parts distilled water;
   (D) 10 to 40 parts horseradish; and
   (E) 6 to 20 parts powdered cayenne pepper.

2. A liniment for topical application in conjunction with manual massage therapy, the liniment comprising:
   (A) 180 parts ethyl alcohol;
   (B) 40 parts methyl hydrate;
   (C) 40 parts distilled water;
   (D) 25 parts horse radish; and
   (E) 13 parts powdered cayenne pepper.

3. A method of preparing a liniment for topical application, comprising:
   (A) preparing a mixture of 90 to 270 parts ethyl alcohol, 20 to 60 parts methyl hydrate, 20 to 60 parts distilled water, 10 to 40 parts horseradish and 6 to 20 parts powdered cayenne pepper;
   (B) sealing in the mixture a container;
   (C) agitating the mixture;
   (D) agitating the mixture twice per day for 10 to 40 days;
   (E) leaving the container stationary for 3 days, thereby allowing the particulate matter to settle; and
   (F) siphoning off a liniment solution from the container.

* * * * *